United States Patent
Hu et al.

(10) Patent No.: US 8,892,195 B2
(45) Date of Patent: Nov. 18, 2014

(54) PHYSIOLOGICAL SIGNAL DETECTION SYSTEM

(71) Applicant: Yu-Feng Hu, Taipei (TW)

(72) Inventors: Yu-Feng Hu, Taipei (TW); Bo-Jau Kuo, Taipei (TW); Shih-Ann Chen, Taipei (TW); Vincent-Ite Hsieh, Taipei (TW)

(73) Assignee: Yu-Feng Hu, Taipei (TW)

( * ) Notice: Subject to any disclaimer, the term of this patent is extended or adjusted under 35 U.S.C. 154(b) by 0 days.

(21) Appl. No.: 14/049,488

(22) Filed: Oct. 9, 2013

(65) Prior Publication Data
US 2014/0221804 A1 Aug. 7, 2014

(30) Foreign Application Priority Data
Feb. 7, 2013 (TW) .............................. 102104766 A

(51) Int. Cl.
*A61B 5/04* (2006.01)
*A61B 5/0408* (2006.01)
*A61B 5/042* (2006.01)

(52) U.S. Cl.
CPC ............... *A61B 5/0408* (2013.01); *A61B 5/042* (2013.01)
USPC ....................................................... 600/509

(58) Field of Classification Search
USPC ....................................................... 600/509
See application file for complete search history.

(56) References Cited

U.S. PATENT DOCUMENTS

| 5,709,213 A | * | 1/1998 | Kruse et al. | 600/509 |
| 2002/0026220 A1 | * | 2/2002 | Groenewegen et al. | 607/4 |
| 2002/0128565 A1 | * | 9/2002 | Rudy | 600/509 |
| 2013/0245473 A1 | * | 9/2013 | Ramanathan et al. | 600/509 |

* cited by examiner

*Primary Examiner* — Robert N Wieland
(74) *Attorney, Agent, or Firm* — Muncy, Geissler, Olds & Lowe, P.C.

(57) ABSTRACT

The present invention provides a handy remote physiological signal detection system, comprising a sensing unit, a stimulation unit and a control unit. The sensing unit includes a detecting electrode, a first surface detection electrode, a second surface detection electrode and a sensing module. The sensing modules is used to detect the signals between the detection electrode and the first surface detection electrode to get an epicardial detection signal, and is also used to detect the signals between the second surface detection electrode and the first detection electrode to get a surface-ECG signal. The stimulus unit includes a stimulating electrode and a stimulus module used to provide a stimulus signal to the stimulating electrode. The control unit includes a user interface and a processing module used to convert the epicardial detection signal and the surface-ECG signal to digital signals and display the digital signals in the user interface. All systems were controlled through the remote system and are small and handy.

13 Claims, 5 Drawing Sheets

PHYSIOLOGICAL SIGNAL DETECTION SYSTEM

CROSS-REFERENCE TO RELATED APPLICATIONS

This Non-provisional application claims priority under 35 U.S.C. §119(a) on Patent Application No(s). 102104766 filed in Taiwan, Republic of China on 02-07-2013, the entire contents of which are hereby incorporated by reference.

FIELD OF THE INVENTION

This invention relates to a signal detection system, and more particularly to a physiological signal detection system.

BACKGROUND OF THE INVENTION

The heart is composed of the cardiac muscle, through the cardiac muscle beats in a regular manner, the heart can be like a pump to transmit the blood to whole body. The cardiac muscle not only can contract, but also can generate conduct current. The organism itself is a good conductor, the current generated from the changes of the cardiac action potential of cardiac conduction fibers, will spread to the whole body from the heart, but different parts of the body include different conducting cells and patterns, the current distribution is not the same.

Different potentials and the sizes of the waveform recorded by different electrodes are called leads. Any two electrodes can be formed as a lead. Metal electrode can be disposed on the organism body limbs, chest, endocardial or epicardial surface for guiding the current of the heart. It is called epicardial electrogram that records the electric signals on the cardiac epicardial surface by the electrodes.

However, the equipment for detecting epicardial or endocardial signals, is fairly complex. The equipment is usually only used to detect a human endocardial electrogram, because the heartbeat of a small animal is very fast and heart volume is very small. It is difficult to detect those in small animals.

Taking a mouse as an example, the method of the prior art to detect the electrophysiological signal of the mouse is to use a very small electrical catheter through a vein or artery to check. However, the technology is very difficult, and it requires large equipment, such as electrical stimulation systems, signal reception and display imaging system, the catheter connection system. The signal is endocardial signals, instead of the epicardial signals. The large equipment is not only expensive, bulky, but also the catheter is easy to damage, and the information collected is limited.

SUMMARY OF THE INVENTION

A physiological signal detection system is provides. The physiological signal detection system is adapted to detect physiological signals of a mouse, such as atrium and ventricle arrhythmic signals, which are not limited herein. The physiological signal detection system of the invention includes a sensing unit, a stimulation unit and a control unit.

The sensing unit of the physiological signal detection system includes a detecting electrode, a first surface detection electrode, a second surface detection electrode, and a sensing module. The sensing module includes a first power supply and a first transceiver.

The detecting electrode is connected to a first position of the mouse. The first surface detection electrode is connected to a ground electrode and a second position of the mouse. The second surface detection electrode is connected to a third position of the mouse. In an embodiment, the second position and the third position are the mouse's limbs, which is not limited herein.

The first power supply provides power to the detecting electrode, the first surface detection electrode, the second surface detection electrode, and the first transceiver.

The sensing module is used to detect signals between the detection electrode and the first surface detection electrode to get an epicardial detection signal. Also, two electrodes in the single needle could be simultaneously recording on the epicardial area, which create the bipolar epicardial signals. The sensing module is also used to detect signals between the second surface detection electrode and the first surface detection electrode to get a surface-ECG signal.

The stimulation unit of the physiological signal detection system includes a stimulating electrode and a stimulus module. The stimulus module includes a second power supply and a second transceiver.

The stimulating electrode is connected to a fourth position of the mouse. The first position and the fourth position are the surface of the mouse's heart, which is not limited herein.

The stimulus module is used to provide a stimulus signal to the stimulating electrode. The second power supply provides power to the stimulating electrode and the second transceiver.

The control unit of the physiological signal detection system is electronically connected to the sensing unit and the stimulation unit. The control unit includes a user interface, a processing module, a storage, and a third transceiver.

The user interface of the control unit provides users to input the stimulus signals or other modulation parameters. The stimulus signals or other modulation parameters are transmitted to the stimulus module of the stimulation unit. Then, the stimulus module processes the stimulus signals or other modulation parameters and transmits them to the stimulating electrode.

The user interface transmits the stimulus signals or other modulation parameters to the second transceiver of the stimulation unit through the third transceiver. The epicardial detection signal and the surface-ECG signal are transmitted to the third transceiver of the control unit through the first transceiver.

The processing module of the control unit converts the epicardial detection signals and the surface-ECG signals to digital signals and displays the digital signals in the user interface.

The stimulating electrode and the detection electrode of the invention can be made by a nerve stimulation needle with single electrode. Compared with the catheter of the prior art, the cost of electrodes in the invention is quite cheap.

In general, electrophysiological cardiac parameters, such as the sinus node, atrioventricular node (A.V. node), atrial and ventricular refractory period, and monitor and induction of cardiac arrhythmias can be completely detected by the physiological signal detection system of the invention.

The physiological signal detection system of the invention combine with remote transmission technology to improve the traditional large electrical stimulation and signaling equipment. The invention can also combine with inexpensive stimulation needle to replace expensive catheter. The invention uses epicardial electrophysiological examination method to replace the surgical method through the blood vessels of the prior art. By this way, the invention can use the single method to execute electrophysiological examination on a plurality of chambers. The technique of the invention is relatively simple, and the size of the equipment of the invention is smaller and portable. The parameters of the stimulation signals can be adjusted by software or users. Even just using a PC system, the control unit still can perform. As a result, the cost of the invention is much less than that of the prior art, and it includes convenience and high commercial value.

DETAILED DESCRIPTION OF THE INVENTION

For clarity of disclosure, and not by way of limitation, the detailed description of the invention is divided into the subsections that follow.

Figure 1:
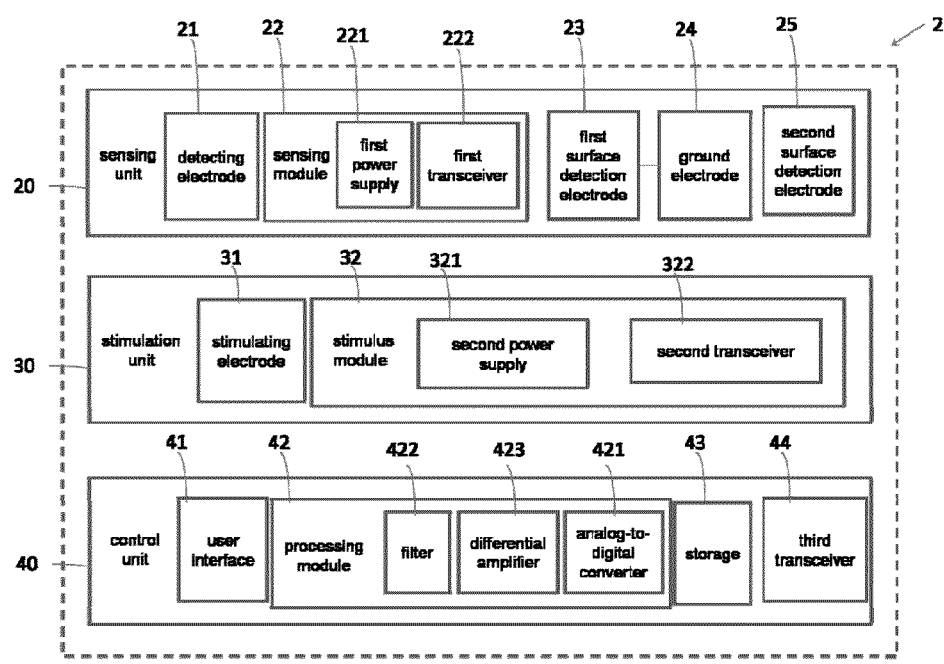
FIG. 1 is a diagram showing a physiological signal detection system of the invention.

FIG. 1 is a diagram showing a physiological signal detection system of the invention. The physiological signal detection system 2 is adapted to detect physiological signals of a mouse, such as atrium and ventricle fibrillation signals, which are not limited herein. The physiological signal detection system 2 of the invention includes a sensing unit 20, a stimulation unit 30 and a control unit 40.

The sensing unit 20 of the physiological signal detection system 2 includes a detecting electrode 21, a first surface detection electrode 23, a second surface detection electrode 25, and a sensing module 22. The sensing module 22 includes a first power supply 221 and a first transceiver 222.

The detecting electrode 21 is connected to a first position of the mouse. The first surface detection electrode 23 is connected to a ground electrode 24 and a second position of the mouse. The second surface detection electrode 25 is connected to a third position of the mouse. In an embodiment, the second position and the third position are the mouse's limbs, which is not limited herein.

The first power supply 221 provides power to the detecting electrode 21, the first surface detection electrode 23, the second surface detection electrode 25, and the first transceiver 222.

In the embodiment described above, three electrodes, the detecting electrode 21, the first surface detection electrode 23, the second surface detection electrode 25, at different positions of the mouse, are used to measure mouse's electrocardiography (ECG). Any two electrodes can be formed as a lead, the three electrodes can be formed as three leads, and the three leads are provided in triangular relationship. One electrode of the three may be taken as a ground electrode, which means to be taken as a reference electrode. In the embodiment described above, the first surface detection electrode 23 is connected to the ground electrode 24, at this time, the first surface detection electrode 23 is taken as a reference electrode. In general, the reference electrode is usually disposed at the farthest position from the heart, because the potential change is minimal, and the error values are also smaller. In addition, if more information is needed, more surface detection electrodes can be also added.

The sensing module 22 is used to detect signals between the detection electrode 21 and the first surface detection electrode 23 to get an epicardial detection signal, a signal of one lead. Also, two electrodes in the single needle could be simultaneously recording on the epicardial area, which create the bipolar epicardial signals. The sensing module 22 is also used to detect signals between the second surface detection electrode 25 and the first surface detection electrode 23 to get a surface-ECG signal, a signal of another lead.

The stimulation unit 30 of the physiological signal detection system 2 includes a stimulating electrode 31 and a stimulus module 32. The stimulus module 32 includes a second power supply 321 and a second transceiver 322.

In an embodiment, the stimulating electrode 31 is connected to a fourth position of the mouse. The first position and the fourth position are the surface of the mouse's heart, which is not limited herein.

In an embodiment, the stimulus module 32 is used to provide a stimulus signal to the stimulating electrode 31. The second power supply 321 provides power to the stimulating electrode 31 and the second transceiver 322. The stimulus signal includes duration time, number of times and intensity of electric shock, which is not limited herein.

The control unit 40 of the physiological signal detection system 2 is electronically connected to the sensing unit 20 and the stimulation unit 30. The control unit 40 includes a user interface 41, a processing module 42, a storage 43, and a third transceiver 44.

The user interface 41 of the control unit 40 provides users to input the stimulus signals or other modulation parameters. The stimulus signals or other modulation parameters are transmitted to the stimulus module 32 of the stimulation unit 30. Then, the stimulus module 32 processes the stimulus signals or other modulation parameters and transmits them to the stimulating electrode 31.

The user interface 41 transmits the stimulus signals or other modulation parameters to the second transceiver 322 of the stimulation unit 30 through the third transceiver 44. The epicardial detection signal and the surface-ECG signal are transmitted to the third transceiver 44 of the control unit 40 through the first transceiver 222, which is not limited to wireless transmission herein.

The processing module 42 of the control unit 40 converts the epicardial detection signals and the surface-ECG signal to digital signals and display the digital signals in the user interface 41.

In an embodiment, the processing module 42 of the control unit 40 includes a filter 422. The filter 422 is used to filter the epicardial detection signals and the surface-ECG signals detected by the sensing unit 20, and noise or unimportant information will be filtered out, only the important information can be kept. The filter 422 of the invention can be low-pass filter, high-pass filter or band-pass filter, which is not limited herein.

In an embodiment, the processing module 42 of the control unit 40 includes a differential amplifier 423. The differential amplifier 423 is used to amplify the filtered epicardial detection signals and the filtered surface-ECG signals. The differential amplifier 423 can amplify the difference voltage between the two input voltages by a fixed gain. As a result, the differential amplifier 423 can enhance the filtered epicardial detection signals and the filtered surface-ECG signals. The differential amplifier 423 of the invention can be a high-speed differential amplifier or a high dynamic range differential amplifier, which is not limited herein.

In an embodiment, the processing module 42 of the control unit 40 includes an analog-to-digital converter 421. The analog-to-digital converter 421 is used to convert the filtered and enhanced epicardial detection signals and the surface-ECG signals to digital signals. Digital signal is the digital representation of discrete-time signal. Digital signal means a group of finite numbers to represent a set of accurate values, and the process is called quantization. That is, the digital signals are quantized epicardial detection signals and the surface-ECG signals. Digital information is often more convenient for subsequent processing or beneficial interpretation.

The stimulus signals, other modulation parameters, the detected epicardial detection signals and the surface-ECG signals or any relative detection information are stored in the storage 43 to subsequent access and query.

Figure 2:
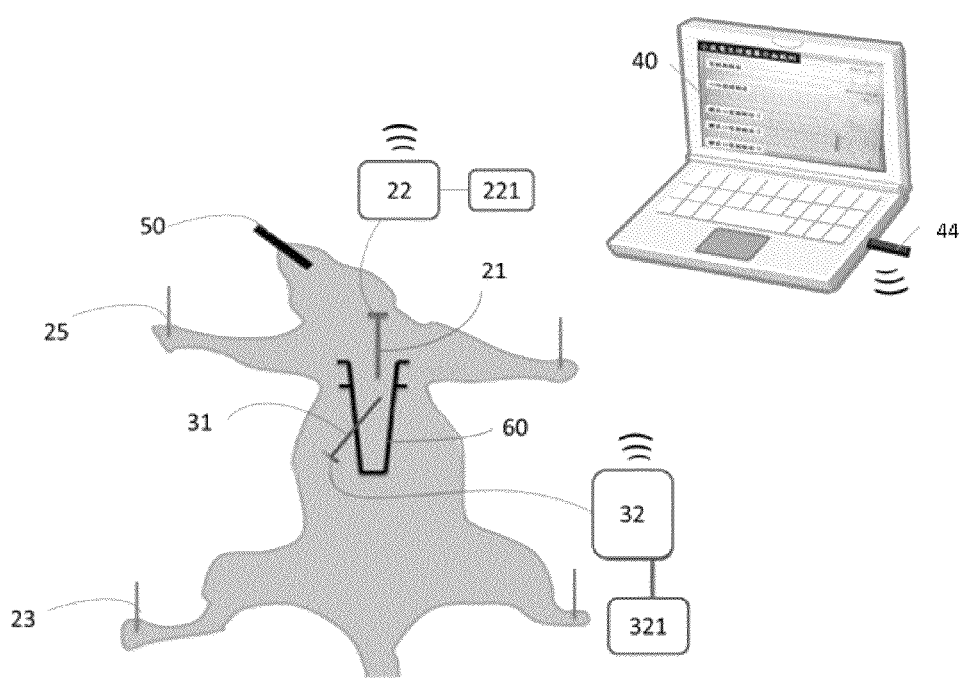
FIG. 2 is a diagram showing a mouse detection by the physiological signal detection system of the invention.

FIG. 2 is a diagram showing a mouse detection by the physiological signal detection system of the invention. First, the mouse needs to be processed by anesthesia, intubation, connecting ventilator 50, and maintain temperature by light equipment. Then, the mouse's right posterior leg is connected to the first surface detection electrode 23, and the mouse's right anterior leg is connected to the second surface detection electrode 25. Besides, the left posterior leg or left anterior leg can be also respectively connected to other surface detection electrodes to provide more lead information. Furthermore, the detection electrode 21 could also be a detection needle of epicardium with two electrodes, and gets a bipolar epicardial detection signal.

Second, the mouse is processed by sternal thoracotomy, and the sternal opening is about 0.3 cm. Then, the detecting electrode 21 and the stimulation electrode 31 are vertically disposed on the surface of the mouse's heart, and are fixed by a bracket 60. Mouse's heart double electrode signals are generated. The stimulating electrode 31 also can electrically stimulate the mouse's heart, which is not limited herein.

Figure 3:
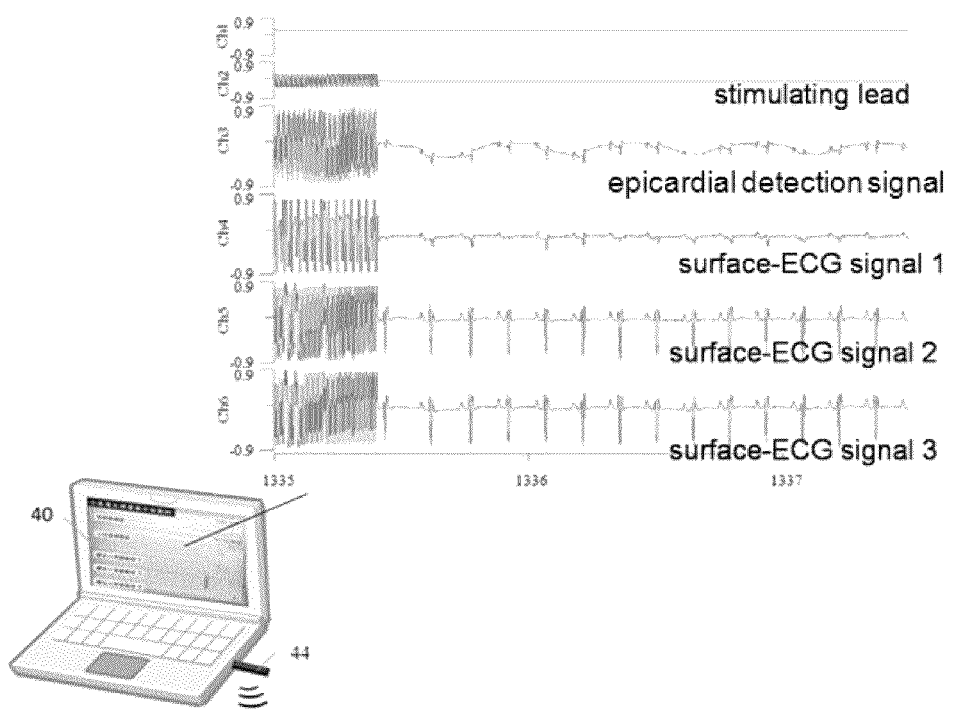
FIG. 3 is a diagram showing the user interface of the invention.

FIG. 3 is a diagram showing the user interface of the invention. The user interface 41 of the control unit 40 provides users to input the stimulus signals or other modulation parameters. The stimulus signal includes duration time, number of times and intensity of electric shock, which can be set by users. The stimulus signals or other modulation parameters are transmitted to the second transceiver 322 of the stimulation unit 30 through the third transceiver 44. Then, the stimulus module 32 processes the stimulus signals or other modulation parameters and transmits them to the stimulating electrode 31. The stimulating electrode 31 stimulates the mouse's heart according to the instructions.

After stimulating the mouse's heart, the sensing module 22 is used to detect signals between the detection electrode 21 and the first surface detection electrode 23 to get an epicardial detection signal. The sensing module 22 is also used to detect signals between the second surface detection electrode 25 and the first surface detection electrode 23 to get a surface-ECG signal, a signal of another lead.

The epicardial detection signal and the surface-ECG signal detected by the sensing module 22 are transmitted to the third transceiver 44 of the control unit 40 through the first transceiver 222. Because the epicardial detection signal and the surface-ECG signal are analog signals, the analog signals will be filtered by the filter 422 of the processing module 42 to drop unimportant information and keep important information. The filtered analog signals are enhanced by the differential amplifier 423 of the processing module 42, and then the filtered and enhanced analog signals are transmitted to the analog-to-digital converter 421 of the processing module 42. The analog-to-digital converter 421 is used to convert the filtered and enhanced signals to digital epicardial detection signals and the surface-ECG signals.

Figure 4:
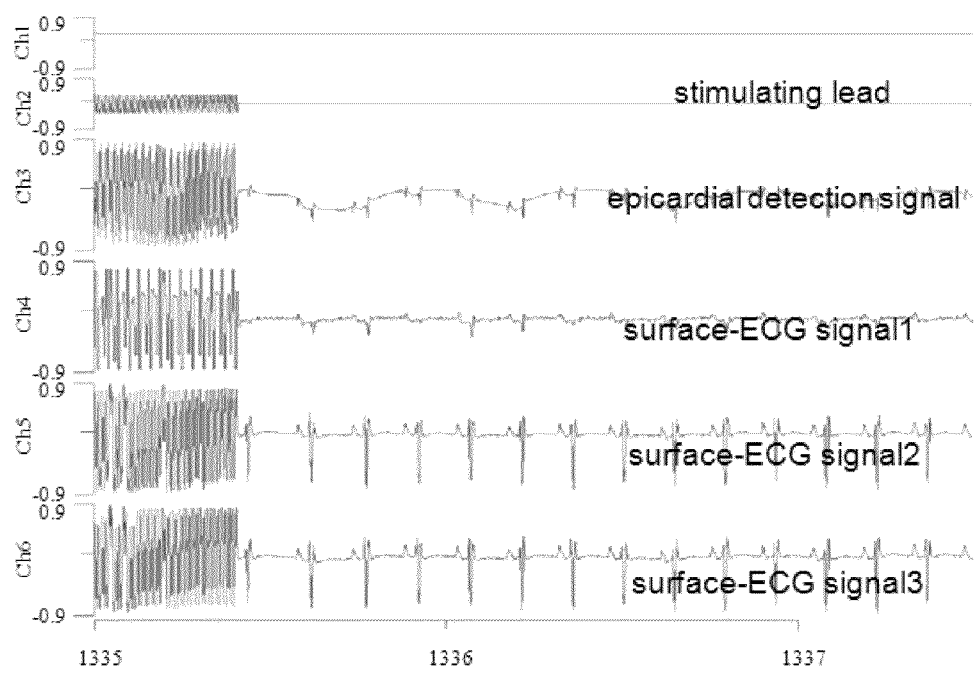
FIG. 4 is a diagram showing the mouse's normal epicardial detection signals and the surface-ECG signals normally detected by the physiological signal detection system of the invention.

FIG. 4 is a diagram showing the mouse's normal epicardial detection signals and the surface-ECG signals normally detected by the physiological signal detection system of the invention. As FIG. 4 shown, unstimulated epicardial detection signals and three surface-ECG signals in three directions are generated through the same time.

Figure 5:
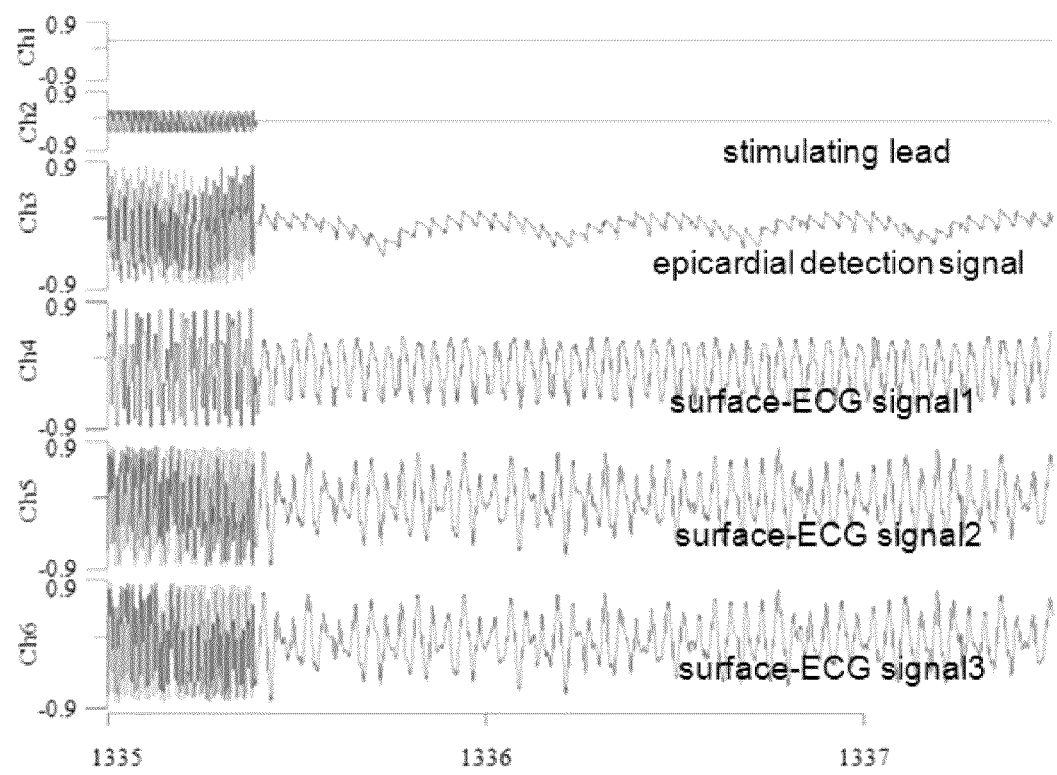
FIG. 5 is a diagram showing mouse arrhythmic signals of ventricular tachycardia signals and the surface-ECG signals sequentially stimulated and detected by the physiological signal detection system of the invention.

FIG. 5 is a diagram showing the mouse's arrhythmic signal (ventricular tachycardia) and the surface-ECG signals sequentially stimulated and detected by the physiological signal detection system of the invention. As FIG. 5 shown, after stimulating by different voltage, stimulated epicardial detection signals and three surface-ECG signals in three directions are generated through the same time.

The stimulus signals or other modulation parameters inputted by the user interface 41, the detected epicardial detection signals and the surface-ECG signals or any relative detection information are stored in the storage 43 to subsequent access and query, which is not limited herein.

The stimulating electrode 31 and the detection electrode 21 of the invention can be made by a nerve stimulation needle with single electrode. Compared with the catheter of the prior art, the cost of electrodes in the invention is quite cheap.

In general, electrophysiological cardiac parameters, such as the sinus node, atrioventricular node (A.V. node), atrial and ventricular refractory period, and monitor and induction of cardiac arrhythmias can be completely detected by the physiological signal detection system of the invention.

The physiological signal detection system of the invention can combine with remote transmission technology to improve the traditional large electrical stimulation and signaling equipment. The invention can also combine with inexpensive stimulation needle to replace expensive catheter. The invention uses epicardial electrophysiological examination method to replace the surgical method through the blood vessels of the prior art. By this way, the invention can use the single method to execute electrophysiological examination on a plurality of chambers. The technique of the invention is relatively simple, and the size of the equipment of the invention is smaller and portable. The parameters of the stimulation signals can be adjusted by software or users. Even just using a PC system, the control unit still can perform. As a result, the cost of the invention is much less than that of the prior art, and it includes convenience and high commercial value.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A physiological signal detection system, adapted to detect a mouse, comprising:
   a sensing unit, comprising:
      a detecting electrode, configured to be connected to a first position of the mouse;
      a first surface detection electrode, configured to be connected to a ground electrode and a second position of the mouse;
      a second surface detection electrode, configured to be connected to a third position of the mouse; and
      a sensing module, detecting signals between the detection electrode and the first surface detection electrode to get an epicardial detection signal, and detecting signals between the second surface detection electrode and the first surface detection electrode to get a surface-ECG signal;

a stimulation unit, comprising:
   a stimulating electrode, configured to be connected to a fourth position of the mouse; and
   a stimulus module, providing a stimulus signal to the stimulating electrode; and a control unit, electronically configured to be connected to the sensing unit and the stimulation unit, comprising:
   a user interface, used to input the stimulus signal; and
   a processing module, converting the epicardial detection signal and the surface-ECG signal to digital signals and display the digital signals in the user interface.

2. The physiological signal detection system according to claim 1, wherein the sensing unit comprises a first power supply.

3. The physiological signal detection system according to claim 1, wherein the sensing unit comprises a first transceiver.

4. The physiological signal detection system according to claim 1, wherein the stimulation unit comprises a second power supply.

5. The physiological signal detection system according to claim 1, wherein the stimulation unit comprises a second transceiver.

6. The physiological signal detection system according to claim 1, wherein the control unit comprises a third transceiver.

7. The physiological signal detection system according to claim 1, wherein the control unit comprises a storage.

8. The physiological signal detection system according to claim 1, wherein the stimulus signal includes duration time, number of times and intensity of electric shock.

9. The physiological signal detection system according to claim 1, wherein the first position and the fourth position are the surface of the object's heart.

10. The physiological signal detection system according to claim 1, wherein the second position and the third position are the object's limbs.

11. The physiological signal detection system according to claim 1, wherein the processing module includes an analog-to-digital converter.

12. The physiological signal detection system according to claim 1, wherein the processing module includes a filter.

13. The physiological signal detection system according to claim 1, wherein the processing module includes a differential amplifier.

* * * * *